(12) United States Patent
Martín Pérez et al.

(10) Patent No.: US 12,416,561 B2
(45) Date of Patent: Sep. 16, 2025

(54) METHOD FOR HYDRODYNAMICS-ASSISTED MULTI-PARAMETER ANALYTE SPECTROMETRY

(71) Applicant: CONSEJO SUPERIOR DE INVESTIGACIONES CIENTIFICAS (CSIC), Madrid (ES)

(72) Inventors: Alberto Martín Pérez, Madrid (ES); Daniel Ramos Vega, Madrid (ES); Montserrat Calleja Gómez, Madrid (ES); Francisco Javier Tamayo De Miguel, Madrid (ES)

(73) Assignee: CONSEJO SUPERIOR DE INVESTIGACIONES CIENTIFICAS (CSIC), Madrid (ES)

( * ) Notice: Subject to any disclaimer, the term of this patent is extended or adjusted under 35 U.S.C. 154(b) by 45 days.

(21) Appl. No.: 18/035,119

(22) PCT Filed: Oct. 21, 2021

(86) PCT No.: PCT/ES2021/070765
§ 371 (c)(1),
(2) Date: May 3, 2023

(87) PCT Pub. No.: WO2022/096764
PCT Pub. Date: May 12, 2022

(65) Prior Publication Data
US 2023/0332994 A1    Oct. 19, 2023

(30) Foreign Application Priority Data

Nov. 5, 2020 (ES) ............................. ES202031115

(51) Int. Cl.
*G01N 15/0205* (2024.01)
*G01B 11/04* (2006.01)
(Continued)

(52) U.S. Cl.
CPC .......... *G01N 15/0211* (2013.01); *G01B 11/04* (2013.01); *G01N 15/1429* (2013.01);
(Continued)

(58) Field of Classification Search
CPC ........... G01N 15/0211; G01N 15/1429; G01N 15/1434; G01N 33/487; G01N 15/02;
(Continued)

(56) References Cited

U.S. PATENT DOCUMENTS 5,211,829 A * 5/1993 Imai ...................... G01N 30/76
204/603
12,135,275 B2 * 11/2024 Martín Pérez ..... G01N 15/1429
(Continued)

FOREIGN PATENT DOCUMENTS

ES        2786848 A1    10/2020
WO    2006034046 A2     3/2006

OTHER PUBLICATIONS

Martin-Perez et al. ("Mechano-Optical Analysis of Single Cells with Transparent Microcapillary Resonators", ACS Sensors, Published Nov. 29, 2019, p. 3325-3332) (Year: 2019).*

*Primary Examiner* — Jennifer D Bennett
(74) *Attorney, Agent, or Firm* — Hayes Soloway P.C.

(57) ABSTRACT

The method uses a suspended resonating microcapillary device, and obtains simultaneously three parameters of the analytes: mass, size and refractive index, enabling the unequivocal classification of the analytes flowing in real time, based on the resonance frequency displacement and the change in reflectivity of the transparent microcapillary. The method comprises the stages of: the obtaining of a measurement of the reflectivity of the sample analytes within the capillary at each moment in time; the obtaining of a mechanical reference signal ($T_t$) of the change in resonance frequency of the microcapillary caused by the sample
(Continued)

analytes over time; and the detection of the passage of the particle through an area of the capillary, and the obtaining of the points of passage of the ends of the analytes through the centre of the illuminated area, obtaining an optical signal $\Delta T$.

3 Claims, 5 Drawing Sheets

(51) Int. Cl.
*G01N 15/02* (2024.01)
*G01N 15/10* (2024.01)
*G01N 15/14* (2024.01)
*G01N 15/1429* (2024.01)
*G01N 15/1434* (2024.01)
*G01N 33/487* (2006.01)

(52) U.S. Cl.
CPC ....... *G01N 15/1434* (2013.01); *G01N 33/487* (2013.01); *G01N 15/02* (2013.01); *G01N 2015/1006* (2013.01); *G01N 2015/1027* (2024.01); *G01N 2015/1029* (2024.01); *G01N 15/14* (2013.01)

(58) Field of Classification Search
CPC .......... G01N 15/14; G01N 2015/1006; G01N 2015/1027; G01N 2015/1029; G01B 11/04
See application file for complete search history.

(56) References Cited

U.S. PATENT DOCUMENTS

2012/0118063 A1  5/2012  Son et al.
2015/0020588 A1  1/2015  Larson et al.

\* cited by examiner

FIG. 1

(STATE OF THE ART)

METHOD FOR HYDRODYNAMICS-ASSISTED MULTI-PARAMETER ANALYTE SPECTROMETRY

CROSS-REFERENCE TO RELATED APPLICATIONS AND PRIORITY

This patent application claims priority from PCT Application No. PCT/ES2021/070765 filed Oct. 21, 2021, which claims priority from Spanish Patent Application No. P202031115 filed Nov. 5, 2020.

OBJECT OF THE INVENTION

The object of the present invention is a method for hydrodynamics-assisted multi-parameter analyte spectrometry, which makes use of a suspended resonating microcapillary device, and which allows obtaining simultaneously three parameters of the analytes: mass, size and refractive index, enabling the unequivocal classification of the analytes flowing in real time, based on the resonance frequency displacement of the resonating microcapillary and its change in reflectivity.

BACKGROUND OF THE INVENTION

High-throughput classification and characterisation of individual micro- and nanoparticles in physiological environments is of particular interest in many different fields, such as environmental monitoring, clinical trials, nanotoxicology, or cell biology. For these purposes, the use of microfluidic devices has been shown to be a robust technique for passive particle classification, which operates with a throughput of up to $10^7$ particles/min, simply taking advantage of the forces exerted by the moving fluid on the particle.

These hydrodynamic forces depend on the shape and size of the particles, which ultimately causes them to move along with the fluid. Although these devices allow the analysis of particles based on geometric properties, static microfluidic devices cannot discern particles in cases where they have the same shape, but are made up of different materials. Therefore, it must be combined with other techniques (for example, optical methods that measure the refractive index) to discern between particles of identical shape.

Moreover, nanomechanical resonators have proven to be a powerful analysis tool, since they can measure multiple physical properties (force, mass, stiffness, etc.) with an extremely high sensitivity, by being able to record changes in the mechanical resonance frequency of a vibrating structure.

However, viscous frictional forces are detrimental to this high sensitivity when the device is submerged in liquid due to the mass of liquid that is displaced during the oscillation cycle. Suspended Microchannel Resonators (SMR) were developed to analyse particles in liquid environments, overcoming the aforementioned problems by merging microfluidics and nanomechanics.

The SMR approach consists of a nanomechanical resonator with an internal microchannel integrated, which allows the resonator to vibrate in a gaseous or vacuum environment, while particles are characterised in the liquid flowing through the microchannel. Since the viscous frictional forces are significantly reduced by placing the liquid inside the resonator, the resolution of the buoyant mass is improved, reaching up to 10 attograms in the latest generation devices that operate in vacuum.

Among SMR devices, transparent microcapillary resonators (TMR) not only combine a nanomechanical resonator with a microfluidic channel, but also allow the measurement of the optical properties of the particles that flow inside same. These devices have proven to be an interesting alternative to SMRs for mass detection, introducing a new source of information about the particle based on its optical characterisation, which makes this mechano-optical particle detection technique a very reliable technique for particle classification, even in cases of particles of similar masses.

Specifically, document US2012/0118063A1 is known, which describes a method for determining the buoyant mass and the deformability of a cell. The method includes introducing the cell into a microchannel resonator comprising a constriction near a distal location in the resonator. A first frequency change in the resonator is monitored, being related to the buoyant mass of the cell. Transit time of the cell through the constriction is measured by monitoring a second frequency change as a result of a change in cell location as it passes through the constriction, whereby deformability is determined from the measured buoyant mass and transit time.

In the works of the state of the art, it is still necessary to have prior information on the size of the particles, acquired by means of other techniques, to calculate a number of parameters of same, such as, for example, the refractive index, or it is necessary to measure each particle twice in liquids of different properties to obtain parameters such as mass density. In particular, the density has been revealed as an interesting parameter for the characterisation of the life cycle of cells in previous works using SMR, due to the relationship of cell density with activity.

Furthermore, current techniques require the measurement of the buoyant mass of the same particle in two media of different density in order to measure its density, which drastically reduces the measurement throughput.

DESCRIPTION OF THE INVENTION

The object of the present invention is a method of hydrodynamics-assisted multi-parameter analyte spectrometry, which makes use of a suspended microcapillary device, particularly a transparent microcapillary resonator (TMR). A fluid circulates through the inside of the device with a number of analytes of interest in suspension, and with the method, it is possible to obtain three parameters measured simultaneously: buoyant mass, particle size and refractive index. These parameters are obtained by measuring the frequency displacement and change in reflectivity of the TMR device measured at different instants of time. This method allows unequivocal classification of analytes flowing in real time.

The proposed method allows the measurement of intensive parameters, such as mass density, for the development of real-time analyte spectrometry in liquids. Specifically, the use of the hydrodynamic analyte approach is proposed to obtain ordered particles with a known position when they pass through the free area of the TMR device. Knowing in advance the position of the analytes inside the tube facilitates the analysis of the signals of frequency mechanical displacement and change in reflectivity caused by the passage of a particle flowing through the TMR, which finally allows knowing the size of the analytes.

This particle diameter measurement is acquired simultaneously with buoyant mass and reflectivity, allowing for a high-throughput triple-parameter analyte characterisation technique as well as calculation of intensive parameters, such as mass density.

As indicated, the method makes use of a sample analysis device of the transparent microcapillary resonator (TMR) type comprising: a substrate; an elongated transparent hollow structure, of the capillary tube type, which has two ends, between which a fluid circulates with the analytes of interest in suspension; two supports, attached to the ends of the capillary tube; a vibration module, preferably a piezoelectric device, coupled to the substrate, suited to produce vibrations therein; a laser that emits a beam of light into the capillary tube; and a photoreceptor suited to receive the beam of light passing through the capillary tube.

The method object of the present invention, which makes use of the described device, comprises a series of stages described below.

First, the laser is actuated, which emits a beam of light that hits the capillary tube containing a sample of interest, the sample being a fluid with analytes in suspension. The beam of light passes through the capillary tube, is reflected by the substrate, and is picked up by the photoreceptor.

The next stage consists of generating a first signal through the photoreceptor and amplifying and filtering said first signal. The amplified and filtered signal is then divided into a modulated component and an unmodulated component.

The unmodulated component of the signal is processed to obtain a measurement of the reflectivity of the capillary tube continuously over time, when a particle passes through the area illuminated by the laser beam, it produces a change in the reflectivity signal (reflected power). From this change in the reflected power, the time difference between the particle entry and exit points to the illuminated area ($\Delta T$) is obtained.

Next, the modulated component of the signal is processed to obtain a reference mechanical signal ($T_r$) of the change in resonance frequency over time caused by the passage of the particle. The maximum variation in frequency depends on the buoyant mass of the particle, and the variation in time depends on the velocity (velocity is obtained as the inverse of the transit time multiplied by the length of the capillary tube).

As a particle passes through the capillary tube, the resonance frequency drops due to the added mass. In documents of the state of the art, only the maximum variation in the resonance frequency and reflected power was analysed, in the present application both curves are adjusted, saving the time it takes to pass: $T_r$ and $\Delta T$. The suspended length of the capillary tube is exactly known, this being understood as the length of the capillary tube comprised between the supports. By knowing the distance and the time it takes to travel said space, the velocity of the particle can be calculated with great accuracy.

Starting from the length of the capillary tube, this length being between the two supports of the device, the mechanical signal and the optical signal, the size of the particle can be calculated as:

$$\phi_{particle} = L_{capillary} \cdot \frac{\Delta T}{T_t}$$

DESCRIPTION OF THE DRAWINGS

To complement the description that is being made and for the purpose of helping to better understand the features of the invention according to a preferred practical exemplary embodiment thereof, a set of drawings is attached as an integral part of said description in which the following is depicted in an illustrative and non-limiting manner.

PREFERRED EMBODIMENT OF THE INVENTION

A preferred embodiment of the method for hydrodynamics-assisted multi-parameter analyte spectroscopy is described below with the aid of FIGS. 1 to 5.

Figure 1:
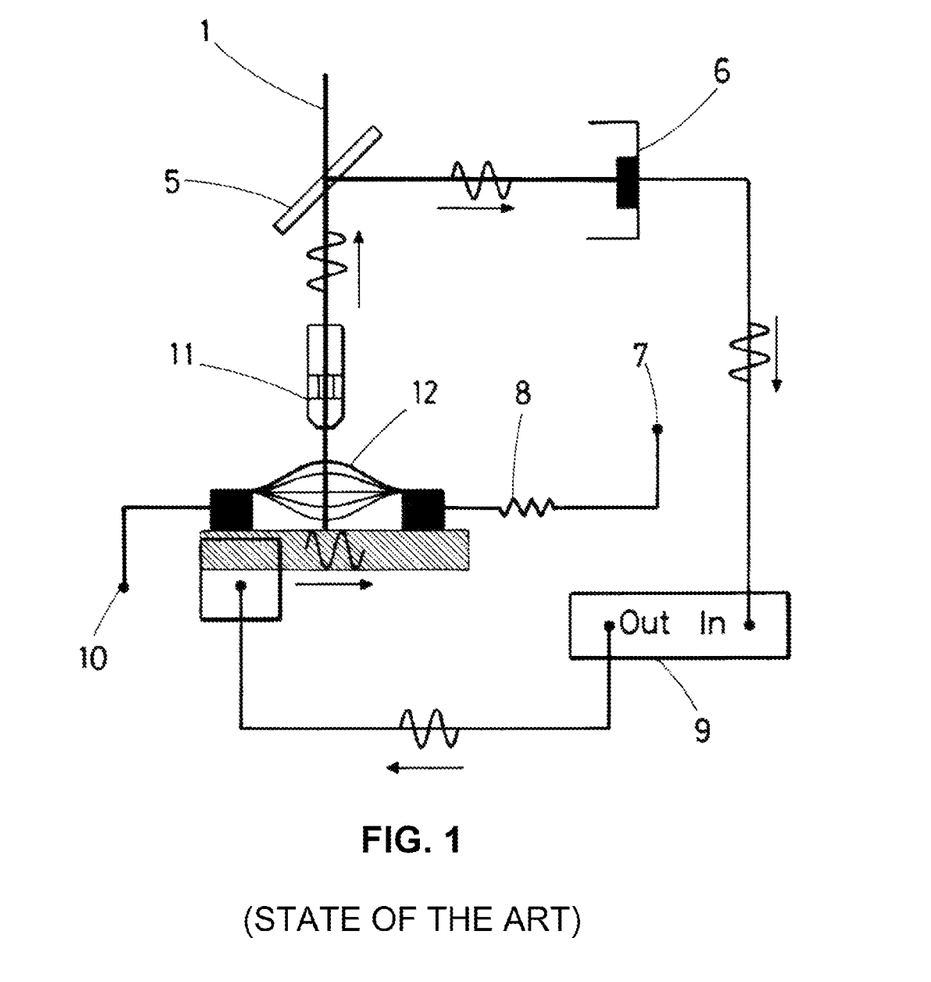
FIG. 1.—Shows a diagram view of a transparent microcapillary resonator (TMR, Transparent Microcapillary Resonator) belonging to the mechano-optical measurement state of the art.
Figure 2:
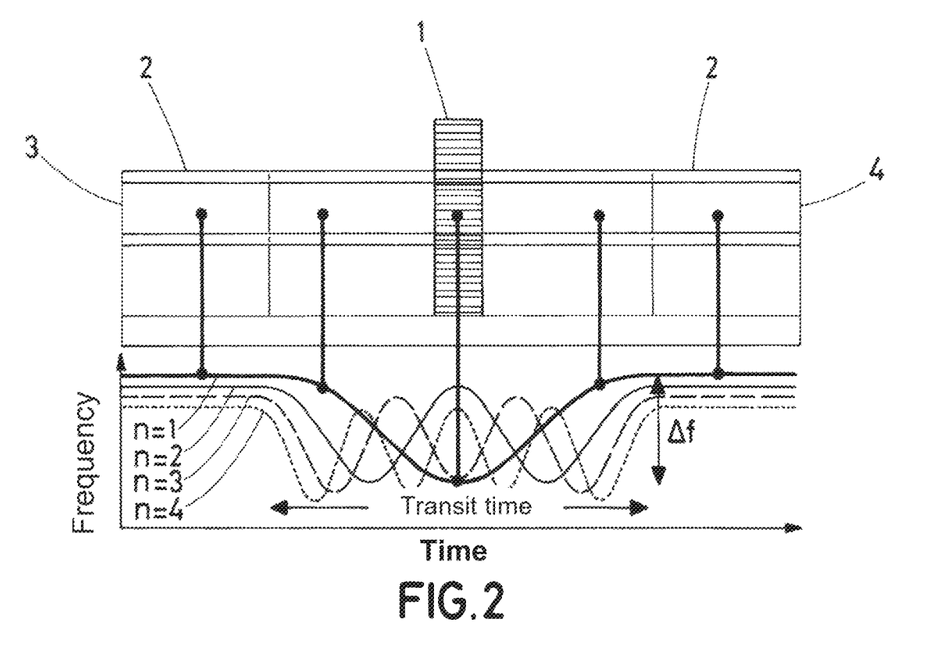
FIG. 2.—Shows a cross-sectional view of the capillary tube positioned between two supports and traversed by the beam of laser light, and in the lower portion a graph with the resonance frequency signal of a particle that traverses the capillary tube.

The method of the invention makes use of a transparent microcapillary resonator (TMR) device (12), shown in a general view in FIG. 1 and in a detailed view in FIG. 2, and comprises: a substrate; an elongated transparent hollow structure, in the form of a capillary tube which has two ends (3, 4), through which a fluid circulates with analytes of interest in suspension; supports (2), coupled to the ends of the capillary tube; a piezoelectric device, coupled to the substrate and making contact with the capillary tube, suited to produce vibrations in the capillary tube; a laser (1) that emits a beam of light; and a photoreceptor (6) suited to receive the beam of light passing through the capillary tube before reaching the photoreceptor (6).

Analytes can be either biological entities, such as cells or bacteria, or inorganic particles of interest.

As shown in FIG. 1, the beam of light coming from a laser (1) passes through a beam splitter (5). After the beam splitter (5) the light is focussed into the capillary tube (12) through a microscope objective (11). Said beam, reflected in the substrate, goes back through the capillary tube and the microscope objective (11) until it reaches the beam splitter (5), which diverts same towards the photoreceptor (6) that picks up the beam of light modified due to the passage through the capillary tube and generates a signal associated both with the movement of the capillary tube and with the properties of the transparent capillary tube and whatever is passing through same at that moment.

The capillary tube has a 44 µm external diameter and a 34 µm inner diameter, and is obtained by local elongation of a fused silica capillary tube having a 350 µm external diameter with a wall thickness of 50 µm. The substrate is made of silicon and the supports (2) are photolithographed polymeric pads, obtaining a suspended region of the capillary tube that is 500 µm long, in which the capillary tube can mechanically oscillate in a manner similar to that of guitar strings, like a resonator.

The mechanical modes of the capillary tube are excited by means of a piezoelectric actuator, while their resonance frequency is monitored in real time by means of an interferometric reading system and a lock-in amplifier (9), as shown in FIG. 1.

This interferometric system also allows the monitoring of the power of the light reflected by the capillary tube to obtain information on the optical properties of the analytes in flow by analysing the scattered light in real time.

In addition, the capillary tube is pressurised by means of a first nitrogen pressure pump (10), which allows the flow to be controlled by establishing a controlled pressure difference through a microfluidic resistor (8).

Finally, the outlet end (4) of the capillary tube is linked to a second nitrogen pump (7), which allows a minimum pressure difference of 5 mbar to be established between the inlet end (3) of the capillary tube and the outlet of the microfluidic resistor (8). The microfluidic resistor (8) allows better control of the flow. This allows control of the rate at which particles of interest or analytes pass through the suspended capillary tube.

For its part, the method object of the present invention, which makes use of the device (12) being disclosed, comprises the stages of:
- the actuation of the laser (1), which emits a beam of light that hits the capillary tube containing a sample and is picked up by the photoreceptor (6),
- the generation of a first signal by means of the photoreceptor (6) and amplification and filtering of the first signal,
- the division of the amplified and filtered signal into a modulated component and an unmodulated component,
- the processing of the unmodulated component (DC) of the signal, by means of a processor to obtain a measurement of the reflectivity of the sample inside the capillary tube at each moment in time;
- the detection of the passage of the particle through an area illuminated by the laser (1), and adjustment to a double Gaussian. The centres of both Gaussians (points 1 and 3 of the dashed curve in FIG. 3) mark the passage of each end of the particle through the centre of the illuminated area, the difference between these points being the value $\Delta T$. Likewise, between points 1 and 3 of the dashed curve there is a maximum value (point 2 on the dashed curve of FIG. 3), corresponding to the centre of the particle passing through the centre of the illuminated area, from which the value of the maximum change in reflectivity can be obtained;
- the processing of the modulated component to obtain a mechanical reference signal ($T_t$) of the change in resonance frequency over time. The change in resonance frequency over time is measured. As a particle passes through the capillary tube, the resonance frequency drops due to the added mass. A curve is adjusted saving the time it takes to pass, lower curve (mechanical signal) of FIG. 3. The exact suspended length of the capillary tube (500 μm) is known since it is manufactured using lithography. By knowing the distance travelled and time, the velocity of the particle can be calculated with great accuracy;
- calculation of particle size as:

$$\phi_{particle} = L_{capillary} \cdot \frac{\Delta T}{T_t}$$

FIG. 2 shows a detailed view of the device (12), wherein a particle flows through a free region of the capillary tube comprised between the supports (2), displacing the resonance frequency signal. The amplitude of this drop ($\Delta f$) depends on the buoyant mass of the particle, while its width (transit time, $T_t$) depends on the velocity of the particle.

Assuming a constant velocity, the analytes flowing, the diameter of which is very small compared to the length of the suspended region of the capillary tube, test the mechanical mode by following their profile. Therefore, the frequency displacement signal tracked in the lock-in amplifier (9) over time for the umpteenth mechanical mode can be written as:

$$f_n(t) = f_{n0} + \frac{\Delta f}{\psi_{n,max}} \left[ \cosh\left[\frac{(2t - 2t_0 + t_T)\beta_n}{2t_T}\right] - \cos\left[\frac{(2t - 2t_0 + t_T)\beta_n}{2t_T}\right] + \frac{\cos\beta_n - \cosh\beta_n}{\sin\beta_n - \sinh\beta_n} \left[ \sin\left[\frac{(2t - 2t_0 + t_T)\beta_n}{2t_T}\right] - \sinh\left[\frac{(2t - 2t_0 + t_T)\beta_n}{2t_T}\right] \right] \right]$$ (Equation 1)

$f_n(t)$ being the frequency of the umpteenth bending mode over time, $f_{n0}$ the natural resonance frequency of the mechanical mode of the resonator, $\psi_{n,max}$ the value of the normalised mechanical mode shape at its maximum amplitude, $t_0$ the time the particle is at the centre of the suspended region and $\beta_n$ the eigenvalue of the mode (the first four eigenvalues are $\beta_n$=4.7300, 7.8532, 10.9956, 14.1372). The dashed lines in FIG. 2 show the frequency displacement induced by a particle in the first four bending modes of the device (12). Without limiting the generality of the foregoing, the fundamental mode is analysed. Adjusting the time frequency displacements to Equation 1 allows either the buoyant mass of the particle or the velocity of the particle to be obtained, which is obtained directly as the inverse of the transit time multiplied by the length of the suspended region of the capillary tube.

The movement of the particle is the result of the force exerted by the liquid on the surface of the particle. Therefore, the dependence of the hydrodynamic force on the size of the particle, which will allow to classify the analytes by their radii, is analysed below.

To demonstrate it experimentally, a homogeneous aqueous suspension of microparticles is introduced into the device (12). If the particles were only subjected to the pulling forces of the fluid in the direction of the flow, they would follow a random distribution in the radial direction of the tube. However, within a laminar flow, each particle also undergoes a displacement orthogonal to the direction of the flow.

This is the consequence of the balance between two lift forces exerted by the fluid on the moving particle: shear gradient (centrifugal) and lift induced by the wall (centripetal). To calculate the equilibrium position of the particles, finite element simulations are performed to calculate the net force in the direction of and on top of the spherical particles having 6.8 μm and 12.4 μm of nominal diameter.

A cylindrical tube the dimensions of which mimic the experimental suspended region of the capillary tube is simulated, and a pressure difference is established between its ends (3, 4). The simulations reveal that the dominant force is always centrifugal, so that in this configuration the equilibrium position is the contact with the capillary tube wall. Therefore, the randomly distributed particles introduced into the capillary tube will be subjected to lift forces, causing all the particles to precipitate on the capillary tube wall. Once precipitated, the thrust and pull force of the particle reaches a steady state. This equilibrium between the hydrodynamic forces causes the particles to cross the suspended area with a constant velocity, allowing the frequency change results to be adjusted to Equation 1. This position of the particles has also been corroborated by optical inspection with a CCD (charge-coupled device) camera.

The device (12) and the measurement system (9) also enable the power of the light reflected (optical signal) by the device (12) to be monitored over time. Therefore, when a particle passes under the region illuminated by the laser (1), it produces a decrease in this optical signal due to scattered light, which can be used to obtain additional information about the particle.

Figure 3:
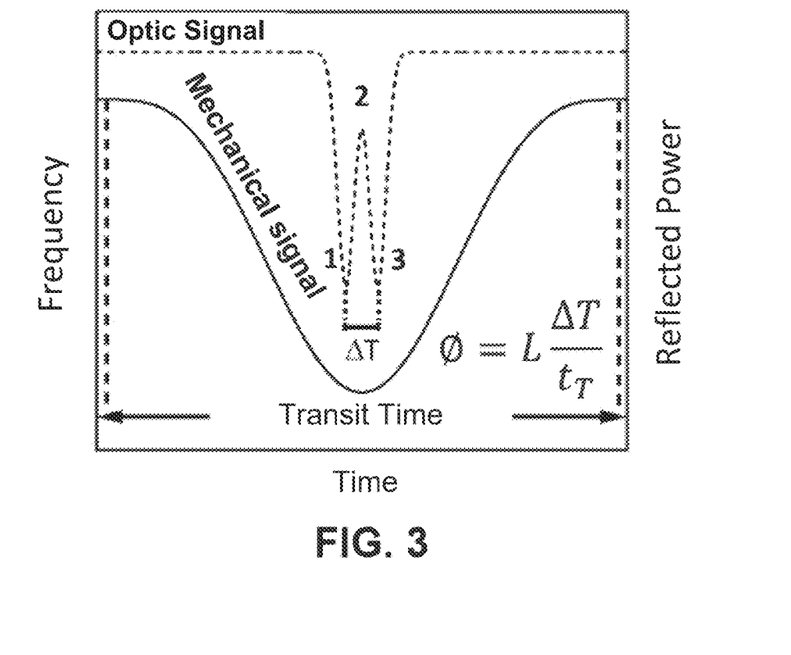
FIG. 3.—Shows a graph in which the optical signal and the mechanical signal of a particle are represented.

This drop in the optical signal, as shown in FIG. 3, consists of a double peak the local maximum of which corresponds to the particle located in the centre of the laser beam (1) while its local minima correspond to the light scattered by the edges of the particle: when each of them is aligned with the centre of the illuminated area. Therefore, given the particle velocity obtained by adjusting the mechanical signal, the particle diameter can be calculated by measuring the time difference between the two local minima of the optical signal.

Figure 5:
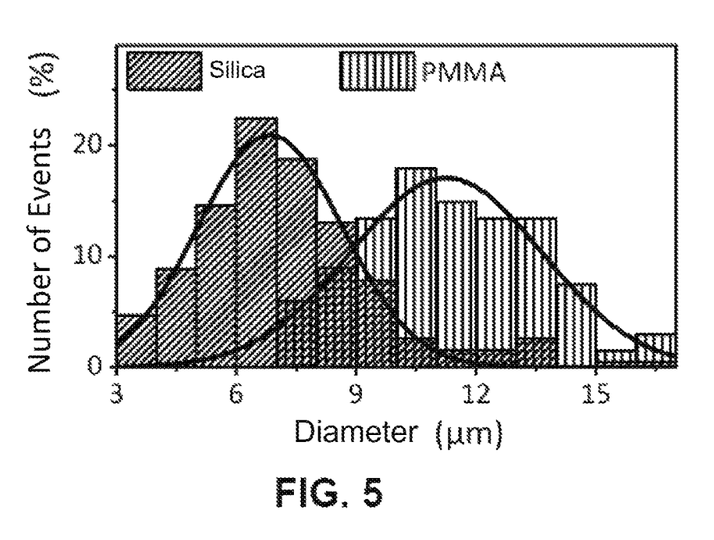
FIG. 5.—Shows the particle size distribution measured for a sample of 67 PMMA particles and 192 Silica particles.

As shown in FIG. 5, a size distribution of 11±2 µm is obtained for PMMA particles and 7±2 µm for silica particles. These values reproduce the results obtained by analysing scanning electron microscope (SEM) images of the same populations 12.4±0.2 µm for the PMMA particles and 6.8±0.4 µm for the silica particles.

Therefore, this method object of the invention enables the simultaneous measurement of three different and independent parameters for each individual particle (buoyant mass, velocity of the analytes and change in reflectivity, $$\frac{\Delta R}{R0_0})$$

with extremely high throughput, up to three hundred analytes per minute. When plotted on a three-dimensional scatterplot, the above analyte mixture can be unequivocally discerned performing highly reliable analyte discernment based on three independent parameters.

In addition, the mass density has been shown to be an interesting parameter for the characterisation of the cell life cycle due to the relationship of cell density with its activity. Cell density is known to vary during the cell life cycle. This is particularly important in human cells, where density remains constant throughout the life cycle, except during mitosis, when cells experience a rapid increase in cell volume with a corresponding decrease in their mass density.

Therefore, there is a dependence on the mass density size, with larger cells showing a lower density. The density of MCF-7 human breast adenocarcinoma cells (mean value 1.11±0.08 g-ml−1), human epithelial breast cells, is measured as a proof-of-concept of the ability of this mechano-optical technique to characterise pathological cells.

Figure 4:
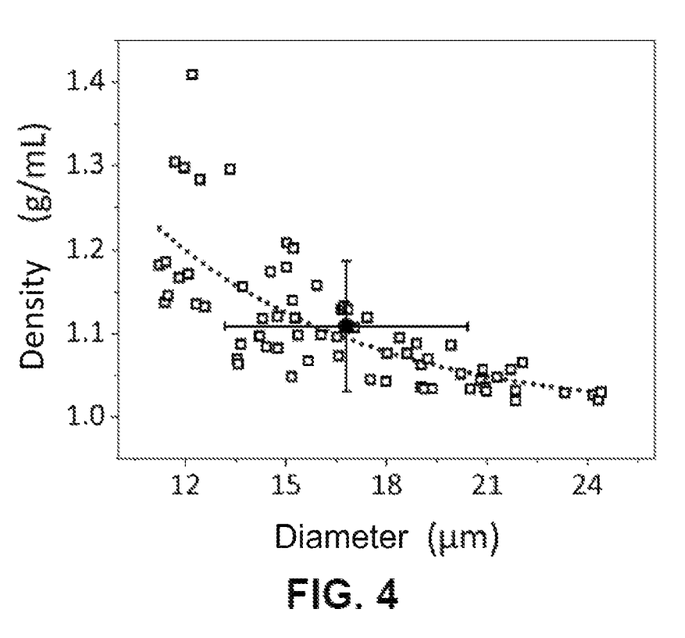
FIG. 4.—Shows experimental measurements of the mass density of individual MCF-7 cells (squares), which correspond to human breast epithelial cells.

As can be deduced from the experimental measurements, shown in FIG. 4, a dependency of the density on their size is observed, which agrees with the results obtained in previous works. The dashed line represents an adjustment of the experimental values, showing the dependency of the measured density on the size. This result demonstrates the capacity of the method of the invention and opens the door to individual studies of the cell cycle.

In conclusion, the present application discloses a method of multi-parameter analyte spectroscopy using suspended microcapillary resonators, simply by following a flexural mechanical resonance mode (preferably the fundamental mode) and the power reflected by the resonator.

Simultaneous measurement of the buoyant mass and the velocity by monitoring the mechanical frequency of the device, as well as the change in reflectivity measured by the optical signal, allow distinction between analyte populations. In the same way, by combining the results of these measurements, other physical parameters of interest such as the size or density of the analytes flowing through the device can be obtained with a high throughput. These parameters have proven to be very interesting for the characterisation of biological entities such as cells.

The invention claimed is:

1. A method of hydrodynamics-assisted analyte spectrometry, which makes use of a transparent microcapillary resonating (TMR) device, which comprises a substrate; a transparent capillary tube with two ends, through which a fluid flows with one or more analytes in suspension; supports coupled to the ends of the capillary tube; a piezoelectric module, coupled to the substrate and making contact with the capillary tube, suited to produce vibrations in the capillary tube; a laser that emits a beam of light; and a photoreceptor suited to receive the beam of light passing through the capillary tube before reaching the photoreceptor; wherein the method comprises the steps of:
    actuation of the laser, which emits the beam of light that hits the capillary tube and is picked up by the photoreceptor,
    generation of a first signal by the photoreceptor and amplification and filtering of the first signal,
    division of the amplified and filtered first signal into a modulated component and an unmodulated component,
    processing of the unmodulated component of the amplified and filtered first signal, and obtaining an optical signal of a measurement of a reflectivity of the analytes at each moment in time,
    detection of a passage of the analytes through an area of the capillary tube illuminated by the laser, and obtaining points of passage of ends of the analytes through a centre of the illuminated area, through the measurement of the reflectivity, for obtaining a time difference ΔT between the analyte entry and exit points to the illuminated area, and
    processing of the modulated component and obtaining a mechanical reference signal of a change in a resonance frequency of the analytes over time as the analytes flow through a free region of the capillary tube and obtaining a transit time ($T_t$) of the analytes through the capillary tube.

2. The method of claim 1, further comprising a final stage of calculating a size of the analytes according to an expression:

$$\phi_{particle} = L_{capillary} \cdot \frac{\Delta T}{T_t}$$

wherein ΔT is the optical signal, $T_t$ is the mechanical reference signal, and $L_{capillary}$ is a free length of the capillary tube comprised between the supports.

3. The method of claim 1, which additionally comprises a stage of calculating a velocity of the analytes as a quotient between $L_{capillary}$ and the mechanical reference signal ($T_t$), $L_{capillary}$ being a suspended length of the capillary tube comprised between the supports.

\* \* \* \* \*